United States Patent

Watts, Jr. et al.

[11] 4,054,605
[45] Oct. 18, 1977

[54] UNSATURATED AMINO ALCOHOLS

[75] Inventors: Lewis William Watts, Jr.; Walter Howe Brader, Jr., both of Austin, Tex.

[73] Assignee: Texaco Development Corporation, New York, N.Y.

[21] Appl. No.: 568,924

[22] Filed: Apr. 17, 1975

[51] Int. Cl.$^2$ .................................... C07C 91/06
[52] U.S. Cl. ........................ 260/584 R; 260/584 C
[58] Field of Search ........................... 260/584 R

[56] References Cited

U.S. PATENT DOCUMENTS

| | | | |
|---|---|---|---|
| 3,350,451 | 10/1967 | Smutny | 260/577 |
| 3,444,202 | 5/1969 | Chung et al. | 260/584 R X |
| 3,470,230 | 9/1969 | Hirsch et al. | 260/584 R X |
| 3,493,617 | 2/1970 | Shryne et al. | 260/584 R X |
| 3,670,032 | 6/1972 | Romanelli | 260/641 X |
| 3,679,748 | 7/1972 | Jones et al. | 260/584 R X |
| 3,752,843 | 8/1973 | Henrick | 260/584 R X |
| 3,755,411 | 8/1973 | Henrick | 260/584 R X |
| 3,755,433 | 8/1973 | Miller et al. | 260/584 R X |
| 3,824,290 | 7/1974 | Henrick | 260/583 H |
| 3,855,322 | 12/1974 | Henrick | 260/584 R X |

Primary Examiner—Daniel E. Wyman
Assistant Examiner—Thomas A. Waltz
Attorney, Agent, or Firm—James L. Bailey

[57] ABSTRACT

This application covers compounds of the formula:

(A)

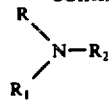

-continued where R is hydrogen or alkanol, $R_1$ is alkanol and $R_2$ is octadienyl or decadienyl;

(B)

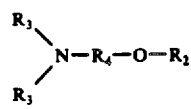

where $R_3$ is alkyl and $R_4$ is alkylene; and (C)

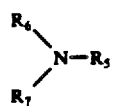

where $R_5$, $R_6$ and $R_7$ are selected from the group consisting of (a) alkanol; (b) —$R_4$— O — $R_2$; (c) (—CH$_2$CH$_2$O—)$_x$R$_2$; and (d)

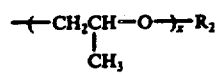

where $R_2$ and $R_4$ are as defined above, x has an average value of 1–50, and the group (b), (c) or (d) occurs in at least one occurrence of $R_5$, $R_6$ or $R_7$.

Also covers a method of preparing the above compounds by reacting the precursor amino alcohols with a C$_4$ or C$_5$ diene compound in presence of a palladium catalyst.

9 Claims, No Drawings

UNSATURATED AMINO ALCOHOLS

BACKGROUND OF THE INVENTION

Reactions involving the catalyzed dimerization of $C_4$ and $C_5$ dienes in the presence of alcohols to form the corresponding ethers are known. One such method involving the preparation of lower alkyl ethers is set out in Takahasi, Tetrahedron Letters, P. 2451 (1967). U.S. Pat. No. 3,670,032 also discloses that both unsaturated alcohols and unsaturated ethers can be formed through the catalyzed dimerization of conjugated aliphatic type diolefins in the presence of water or a lower alkyl alcohol or mixtures thereof.

While treatment of alcohols or amines with dienes is known, it is believed that heretofore there is no reference to the catalytic addition of $C_4$ and $C_5$ dienes to amino alcohols. More particularly, there is no known procedure to selectively alkylate the amino function of an amino alcohol of the type set out hereinafter.

SUMMARY OF THE INVENTION

Now, in accordance with the present invention, it has been found that certain amino alcohols can be catalytically reacted with $C_4$ and $C_5$ diolefins to produce amino ethers. In brief, the compounds of the invention so formed are as follows:

A compound having a formula selected from the group consisting of:

(A)

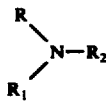

where R is hydrogen or alkanol, $R_1$ is alkanol and $R_2$ is octadienyl or decadienyl;

(B)

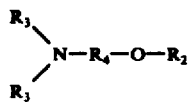

where $R_3$ is alkyl and $R_4$ is alkylene; and (C)

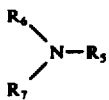

where $R_5$, $R_6$ and $R_7$ are selected from the group consisting of (a) alkanol; (b) $-R_4-O-R_2$; (c) $(-CH_2CH_2O-)_xR$; and (d)

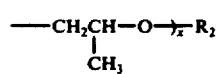

where $R_2$ and $R_4$ are as defined above, x has an average value of 1–50, and the group (b), (c) or (d) occurs in at least one occurrence of $R_5$, $R_6$ or $R_7$.

The above compounds are prepared by reacting a $C_4$ or $C_5$ diolefin with the precursor amino alcohol by means of a catalytic dimerization reaction. The catalyst involved is a palladium catalyst whose activity may be promoted or activated by a phosphine compound.

DESCRIPTION OF THE PREFERRED EMBODIMENTS

The above defined compounds are prepared by reacting the precursor alcohols with butadiene, 1,3-pentadiene or isoprene in presence of a palladium catalyst.

The starting amino alcohol reactants then have the following formulae:

(1)

where R is hydrogen or alkanol and $R_1$ is alkanol;

(2)

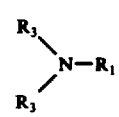

where $R_3$ is alkyl and $R_1$ is alkanol; and (3)

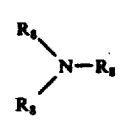

where $R_8$ is selected from the group consisting of (a) $R_1$,
(b) $-(CH_2CH_2O)_xH$, and
(c) 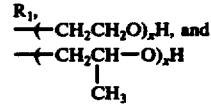

where $R_1$ is alkanol and x is an average number of 1–50.

It is also believed that many of the fully saturated or hydrogenated derivatives of the just described unsaturated compounds are also novel.

In view of ready reactivity of the $C_4$ or $C_5$ diene compound with alcohol groups as set out in U.S. Pat. No. 3,670,032, it was quite surprising to discover that the amino function of the amino alcohol reactants is exclusively alkylated to form the N-substituted octadienyl or decadienyl compound. The reaction goes exclusively N-alkylation and substantially no ether compound is formed. On the other hand when the amino alcohol has the nitrogen atom fully substituted via alkyl or alkanol groups, ether formation is observed to the exclusion of any amine quaternization.

Representative amino alcohols which may be utilized in the process here include monoethanolamine, N-nonylethanolamine, diethanolamine, N-ethanolamine, triethanolamine, and ethylene oxide and propylene oxide adducts of any of the foregoing alkanolamines or others. Such ethylene and propylene adducts of amino alcohols are well known materials, and may be made via conventional techniques, such as set out in U.S. Pat. No. 3,798,184 describing amino alkylation, which techniques may also be applied here in a variety of ways. For example, the amino alcohols above may be reacted with the diene compound, and the resultant product ethoxylated or propoxylated. In like manner, single amino alcohols may be first ethoxylated or propoxylated, and thereafter the unsaturated ether formed.

With particular regard to the amino alcohol reactants set out above, it is preferred that when R or $R_1$ is an alkanol group, it be a lower alkanol group containing 1-4 carbon atoms. Likewise preferred reactants are those where the $R_3$ alkyl group ranges in carbon content from 1-4 carbon atoms and is methyl, ethy, isopropyl, n-propyl, isobutyl, n-butyl, and t-butyl.

With respect to the final products as defined by the generic formulae above, $R_4$ alkylene groups may be either branched or straight chain alkylene groups such as methylene, ethylene, n-propylene, isopropylene, n-butylene, etc. Again, it is preferred that $R_4$ alkylene groups contain 1-4 carbon atoms.

The palladium catalyst which is normally employed in amounts ranging from about 0.01 to about 2 grams of catalyst per mol of diene, may be in any form. Finely divided elemental metal, complexes, salts, and the like may be used. It is generally preferred that the metal catalysts be soluble in the reaction medium. Suitable salt forms include the halides, such as the chlorides; nitrates; phosphates; sulfates; acetates; acetylacetonates; octoates; and the like. Exemplary are palladium acetate, palladium acetylacetonates, palladium chloride, palladium octoate and the like. Most preferred is palladium acetate.

In a greatly preferred embodiment, a phosphine promoter or activator is employed as part of the catalyst system. Typical phosphine compounds are $R_1$, $R_2$, $R_3 P$ wherein $R_1$, $R_2$ and $R_3$ are monovalent, substituted or unsubstituted organic radicals having from 1-12, preferably 1-10 carbon atoms per molecule. Preferably $R_1$, $R_2$ and $R_3$ are monovalent acyclic or alicyclic alkyl radicals having from 1-8, preferably 1-4 carbon atoms, such as methyl, propyl, isobutyl, cyclohexyl, etc.; phenyl radicals; monovalent alkylaryl radicals having from 7-12, preferably 7-10 carbon atoms, e.g., tolyl, xylyl, ethylphenyl, etc.; and monovalent aralkyl radicals having from 7-12, preferably 7-10 carbon atoms, such as benzyl, ethylbenzyl, diethylbenzyl, etc. Most preferred are triphenylphosphine and trimethylphosphine compounds. The catalyst promoters again may be utilized in varying amounts. Thus the concentration of the promoter within the reaction zone may vary from about 0.01 to about 2.0 grams per mol of diene reactant.

The catalyzed dimerization of the diolefins in the presence of an amino alcohol may be carried out preferably under pressure by charging an appropriate amino alcohol, the diene itself, and a catalytic quantity of palladium catalyst to a suitable reaction vessel, such as an autoclave. The mixture is then heated using conventional techniques, until the desired product is produced.

The reaction is carried out at temperatures generally in the range from about 20° to about 150° C, preferably from about 50° to about 120° C.

The time required to produce the desired product can vary widely and is, dependent upon the particular compounds employed, reaction conditions, and the like. Generally the time employed is in the range from about ¼ hour to about 36 hours, and more often is completed in ½ - 10 hours. In a typical reaction scheme, the reaction is considered complete in ½ - 5 hours.

The use of inert diluents is not necessary to our process but can be employed. If inert diluents are employed, hydrocarbons containing from about 4 to about 12 carbon atoms per molecule such as benzene, toluene, and the like are preferred.

The relative ratios of the starting reactants employed can, of course, be widely varied. To provide the theoretical optimum yields at least 2 mols of diene are provided per reactive hydrogen of the amino atom of the amino alcohol. In the usual situation, an excess of diene is employed. In case di-N-alkylation is desired at least 4 moles of diene must be employed per mol of amino alcohol. It has been found however, that once mono-N-alkylation has proceeded, it is more difficult to drive the reaction to di-N-alkylation and the mono-alkylated product is achieved in good yields to the exclusion to the di-alkylated product. When the nitrogen atom of the amino alcohol is fully substituted, oxygen alkylation then takes place to produce the unsaturated amino ethers. Again, the amount of diene compound necessary to achieve O-alkylation is simply calculated, and again usually an excess of diene is desirable.

The unsaturated compounds produced according to the process of the invention have many and varied uses. As one example, they may be hydrogenated in liquid phase in the presence of a typical hydrogenation catalyst such as nickel, platinum, or palladium and reduced to a corresponding saturated amino alcohol or amino alcohol ethers. These products in turn can be reacted with phthalic anhydride to form useful polyvinylchloride plasticizing materials. The saturated compounds can also be used in paint or varnish formulations, in cosmetics, etc. The unsaturated amino alcohol products may be used as such as surfactants or alkoxylated in the usual manner to produce active surfactant compositions.

The invention will be further understood by reference to the following examples.

EXAMPLE I

A mixture of monoethanolamine (100 ml), 27 gms butadiene, 0.25 gm palladium acetate, and 1.0 gm triphenylphosphine was charged to a 300 ml stainless steel autoclave, flushed with nitrogen, and then heated at 90° C for 1-¾ hours. Filtration of the crude reaction mixture afforded a bright yellow-green solid and 124 gms of a pale brown filtrate. Spectral data (nmr, ir, and glc) indicated the major product formed was the mono-N-octadienylated monoethanolamine, I. In particular, no evidence for O-alkylation (i.e., for the formation of corresponding octadienylated ether) was observed.

The reaction proceeded as follows:

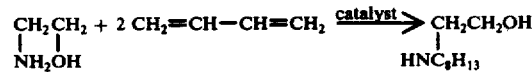

EXAMPLE II

In a similar manner as described in Example I, diethanolamine (100 ml), butadiene (27 gms), palladium acetate (0.25 gm), and triphenylphosphine (1.0 gm) were charged to a 300 ml capacity autoclave, and heated at 90° C for 1-¾ hours. Filtration followed by removal of low boiling components in vacuo gave the nitrogen alkylated octadienyl derivative II.

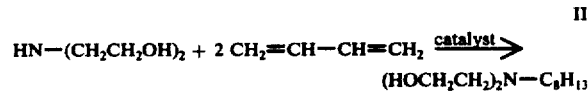

EXAMPLE III

According to the procedure of Example I, upon heating a mixture of butadiene (27 gms), palladium acetate, triphenylphosphine, and N,N-dimethylethanolamine (80 ml) at approximately 90° C for 2 hours there was ultimately isolated a product which had structure III on the basis of analytical and spectral data.

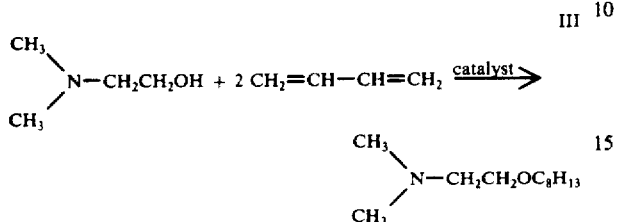

EXAMPLE IV

Upon warming a mixture of butadiene (60 gms), palladium acetate (0.25 gm), triphenylphosphine, and triethanolamine at approximately 110° C for 1 hour in a 300 ml autoclave, the pressure decreased from a maximum of 230 psig to 32 psig.

Removal of light boiling material under reduced pressure gave rise to a material having structure IV, basis analytical and spectral data. Again, exclusive oxyen alkylation occurs upon treatment of the tertiary-aminoalcohol with butadiene.

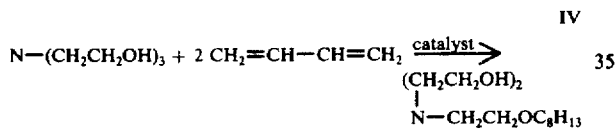

EXAMPLE V

To a 1400 ml rocking type autoclave there was charged 250 gms (4.64 mole) butadiene, 327 gms (3.11 moles) diethanolamine, 0.5 gms palladium acetate, 2.0 gms triphenylphosphine, and 3.6 gms zinc acetate. The resulting mixture was heated to 100° C, at which point the pressure was 238 psig. During the ensuing exothermic reaction (maximum temperature 142° C), the pressure decreased to 25 psig over a period of approximately 14 minutes. Removal of low boiling materials under reduced pressure (1.0 mm at 85° C pot temperature) provided a pot residue (472 gms) which, according to both analytical (hydroxyl number 587, % nitrogen 7.57) and spectral data (nmr, ir, and gpc) was the desired nitrogen alkylated derivative II.

EXAMPLE VI

Interaction of butadiene (85 gms), palladium acetate (0.25 gm), triphenylphosphine (1.0 gm), and 3.6 gms zinc acetate with the 2 mole propylene oxide adduct of monethanolamine in the presence of 30 ml pyridine ultimately provided for the formation of the desired adduct V, i.e., the oxygen alkylated adduct.

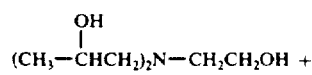

(V)

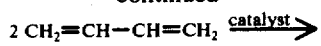

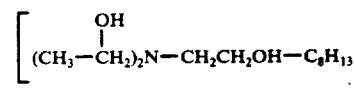

The invention is hereby claimed as follows:

1. A compound having a formula:

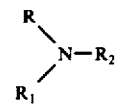

where R is hydrogen or alkanol, $R_1$ is alkanol and $R_2$ is octadienyl or decadienyl.

2. The compound of claim 1 where R is hydrogen and $R_1$ is lower alkanol containing 1–4 carbon atoms.

3. The compound of claim 1 wherein R and $R_1$ are lower alkanol containing 1–4 carbon atoms.

4. A compound according to claim 2 which is

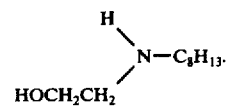

5. A compound according to claim 3 which is

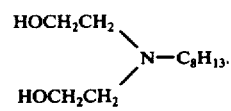

6. A process of preparing a compound having a formula

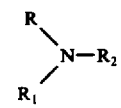

where R is hydrogen or alkanol, $R_1$ is alkanol and $R_2$ is octadienyl or decadienyl which comprises the step of reacting a compound having a formula

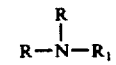

where R is hydrogen or alkanol and at least one occurrence of R is hydrogen and $R_1$ is alkanol with a diene compound selected from the group consisting of butadiene, 1,3-pentadiene, and isoprene in the presence of a palladium catalyst.

7. The process of claim 6 where said reaction is carried out in the presence of a phosphine catalyst promoter.

8. The process of claim 6 wherein said reaction is carried out at a temperature ranging from about 20 to about 150° C for a period of time ranging from about ¼ hour to about 10 hours.

9. The process of claim 8 wherein said palladium catalyst is present in an amount ranging from about 0.01 gram to about 2 grams per mol of diene reactant.

* * * * *